(12) United States Patent
Young

(10) Patent No.: US 11,169,034 B2
(45) Date of Patent: Nov. 9, 2021

(54) METHOD OF MEASURING THE EFFECT OF MECHANICAL STRAIN ON FERROMAGNETIC FIBERS

(71) Applicant: Lateral Logic Limited, Wantage (GB)

(72) Inventor: Robin Young, Lincoln (GB)

(73) Assignee: Lateral Logic Limited, Lincoln (GB)

( * ) Notice: Subject to any disclaimer, the term of this patent is extended or adjusted under 35 U.S.C. 154(b) by 356 days.

(21) Appl. No.: 16/257,994

(22) Filed: Jan. 25, 2019

(65) Prior Publication Data
US 2019/0226924 A1 Jul. 25, 2019

(30) Foreign Application Priority Data

Jan. 25, 2018 (GB) ..................................... 1801223

(51) Int. Cl.
| | | |
|---|---|---|
| *G01L 1/12* | (2006.01) | |
| *G01N 33/38* | (2006.01) | |
| *G01N 3/08* | (2006.01) | |
| *G01N 33/00* | (2006.01) | |
| *C04B 14/48* | (2006.01) | |
| *C04B 28/02* | (2006.01) | |
| *G01N 27/84* | (2006.01) | |
| *C04B 111/00* | (2006.01) | |

(52) U.S. Cl.
CPC ................ *G01L 1/12* (2013.01); *C04B 14/48* (2013.01); *C04B 28/02* (2013.01); *G01N 3/08* (2013.01); *G01N 27/84* (2013.01); *G01N 33/383* (2013.01); *C04B 2111/00422* (2013.01); *G01N 2033/0003* (2013.01); *G01N 2203/0062* (2013.01); *G01N 2203/0067* (2013.01); *G01N 2203/0075* (2013.01); *G01N 2203/0244* (2013.01); *G01N 2203/0635* (2013.01)

(58) Field of Classification Search
None
See application file for complete search history.

(56) References Cited

U.S. PATENT DOCUMENTS

| | | | | |
|---|---|---|---|---|
| 3,727,982 | A * | 4/1973 | Itoh ......................... | E04G 23/08 299/14 |
| 4,062,913 | A * | 12/1977 | Miller ..................... | B28B 1/523 264/437 |
| 5,447,564 | A * | 9/1995 | Xie ......................... | C04B 28/02 106/644 |
| 7,537,054 | B2 * | 5/2009 | Reddy ..................... | C04B 28/02 166/292 |
| 10,161,907 | B2 * | 12/2018 | Fiala ...................... | G01N 27/82 |

* cited by examiner

*Primary Examiner* — Andre J Allen
*Assistant Examiner* — Jermaine L Jenkins
(74) *Attorney, Agent, or Firm* — Maine Cernota & Rardin

(57) ABSTRACT

Disclosed herein is a concrete material comprising between 0.5% and 10% ferromagnetic fibres. Also disclosed herein is a method for measuring the strain state of a concrete material, the method comprising forming solid concrete containing between 0.5% and 10% ferromagnetic fibres in a random distribution throughout the concrete, applying an oscillating EM current to the concrete, and detecting the associated EM fields within the concrete. Also disclosed herein is the use of an oscillating EM current field to measure the strain state within a concrete material comprising between 0.5% and 10% ferromagnetic fibres.

9 Claims, 4 Drawing Sheets

METHOD OF MEASURING THE EFFECT OF MECHANICAL STRAIN ON FERROMAGNETIC FIBERS

RELATED APPLICATIONS

This application claims the benefit of GB Patent Application GB1801223.7, filed Jan. 25, 2018. This application is herein incorporated by reference in its entirety for all purposes.

FIELD OF THE INVENTION

The present invention relates to concrete materials comprising ferromagnetic fibres and methods of measuring strain within said materials.

BACKGROUND OF THE INVENTION

Concrete is essential for transport (bridges and tunnels in roads, railways and ports) as well as buildings and capital projects in water and energy systems.

Load bearing capacity and condition monitoring in large or critical concrete structures is increasingly desirable, particularly in Building Information Management Systems (BIMS). This is because it facilitates the provision of real-time building conditions and allows a competitive advantage through reduced construction cost, reduced cost of building ownership and asset life extension. The sensing of concrete condition (strain, stress, micro-cracking, etc) is central to the effective deployment of Building Information Systems (BIMS).

Over the past decade there has been an increasing trend to replace the traditional steel reinforcing bars ("rebar") with short steel fibres distributed throughout the concrete matrix. The addition of steel fibre to a concrete mix can confer sufficient strength, pseudo-plasticity and toughness to allow structures to be constructed without rebars. The use of Steel Fibre Reinforced Concrete (SFRC) removes the need to assemble a reinforcing "cage" which is a time consuming, error prone, process that carries a significant risk to construction personnel. Austenitic grades of stainless steel fibres have been adopted by the construction sector as these provide good corrosion resistance, improving the durability and design life of SFRC structures. However it makes detection of stresses and strains within the concrete difficult to monitor accurately as existing methods lack the range and sensitivity to provide accurate and reliable data. This is the case even when sensors are embedded within the concrete for providing in situ measurement of stresses and strains. On top of this, the sensors are costly and prone to corrosion when embedded.

Some examples of the use of embedded sensors are provided in patents CN101713638, KR20090071422, WO2015181422. The sensors may be optical fibre gauges, vibrating wire gauges or strain gauges which all require prior installation at the point of manufacture and interconnect for interrogation. Non-embedded solutions include external strain gauges, mechanical strain gauges and digital image correlation.

There has now been devised a concrete material and a method for measuring the strain within said concrete which substantially overcomes and/or mitigates the above referenced and/or other short comings associated with the prior art.

SUMMARY OF THE INVENTION

In a first aspect of the invention there is provided a concrete material comprising between 0.5% and 10% by volume ferromagnetic fibres.

In a second aspect of the invention there is provided a method for measuring strain within a concrete material, the method comprising: a) forming solid concrete containing between 0.5% and 10% ferromagnetic fibres in a random distribution throughout the concrete, b) applying a magnetic field to the concrete to induce a magnetization within the concrete, and c) measuring the magnetization within the concrete induced by the magnetic field.

In a third aspect of the invention there is provided use of a magnetic field to measure the effect of mechanical strain on ferromagnetic fibres contained within a concrete material, wherein the fibres are included within the concrete in random distribution and at a concentration of between 0.5% and 10%.

The concrete material according to the first aspect is advantageous because it is optimised for detection by probes used for measuring magnetic properties and hence provide information about the condition of the concrete. This allows for more innovative and efficient design of the concrete. This will allow life extension of critical infrastructure or confirmation of integrity after damage events or degradation (impact, subsidence, earthquake, blast). Further benefits are optimal value from investment, reduction in rebar, reduced operating costs through easier inspection and life extension enabled by condition validation and through life inspectability. The levels included above are advantageous primarily for poured as well as sprayed compositions of concrete.

The method according to the second aspect is advantageous primarily because it enables load monitoring and damage detection from the surface of any large concrete structure reinforced with steel fibres. It also does so non-destructively and without having to embed sensors into the concrete. The method according to second aspect also allows the detection of the onset of micro-cracking damage in fibre reinforced concrete prior to failure.

In conventional circumstances, when load is applied to concrete, the load is transferred to any reinforcement placed within the concrete. The reinforcement acts to hold the concrete together. However if load increases then the reinforcement pulls out of the concrete or the reinforcement breaks itself. The method as described above is advantageous because it enables detection of the onset of microcracking before it leads to instability in the concrete and catastrophic failure.

The use according to the third aspect is advantageous primarily in substantially the same manner.

Preferably the concrete material comprises between approximately 1% and approximately 2% ferromagnetic fibres. This allows application for poured concrete compositions.

Preferably the ferromagnetic fibres are stainless steel as this provides corrosion resistant reinforcement to the concrete, and strength.

The length of the fibres for the purposes of this invention is provided at approximately 20 mm to approximately 50, preferably approximately 30 mm to approximately 40 mm, more preferably at 36 mm or less.

The fibres may have a width of up to 4 mm. The width and length dimensions stated above are advantageous primarily as they allow a higher concentration of fibres in the concrete, which in turn means that it is possible to get a stronger detection response. This is also advantageous because a fibre with increased width provides a) improved coupling with any electromagnetic field because eddy currents induced are less constrained and b) improves the mixing processability of concretes with higher volumetric loadings of fibre.

The concrete may comprise a cement content of 325 kg/m3 plus or minus 20%.

The concrete material may include but is not limited to mortar (i.e. concrete but without large aggregate). This has benefits in some circumstances as it allows for easier inclusion of fibres within the concrete material towards the upper percentage range described above.

Preferably the concrete material comprises an aggregate, as this makes the concrete material stronger. More preferably, the aggregate content has a maximum size of 20 mm. This is to create maximum strength in the concrete, without over weakening the concrete due to the aggregate content and allow for sufficient inclusion of fibres.

In the method of the invention, steps b) and c) may be performed using a magnetic permeability probe. Such a probe has the advantage that steps b) and c) can be performed using a single device.

In step b) of the method, the magnetic field may be applied by placing a current carrying coil (electromagnet) or permanent magnet in contact with or close to the fibre containing concrete. The magnetic field applied may be an oscillating, static or quasistatic electromagnetic field. In step c) of the method the detection of the magnetization within the fibre containing concrete may be performed by using a Hall probe or by measuring the reactance in the current carrying coil The frequency of any oscillating magnetic fields is preferably 5 kHz but could be in the range of 1 to 50 kHz Conventional ferromagnetic materials are those, as the name suggests, which exhibit ferromagnetic qualities. Ferromagnetic materials are known to have certain alloying constituents of different elements, such as Carbon, or Chromium. This changes the strength or corrosion resistant properties of the material. In other examples, Silicon is used as an alloying component with Iron for example in the Iron core of transformers. In such instances, the Silicon is known to absorb the vibration which occurs routinely within the Iron core of the transformers and therefore prevents energy losses. However if Silicon is used as an alloying component with Iron in too higher proportion, then the Iron-Silicon alloy becomes brittle. There has now been devised a ferromagnetic fibre which substantially overcomes and/or mitigates these and other disadvantages associated with the prior art.

In a fourth aspect of the invention there is provided a ferromagnetic fibre comprising alloying additions of Carbon, Silicon, Manganese, Chromium and Nickel, wherein the Silicon is provided at a level within the fibre of approximately 1% to approximately 8%.

As with any fibres, the ferromagnetic qualities of the fibre vary with applied strain. This is known as the magnetostrictive effect in which applied strain causes magnetic domain movement which affects magnetic permeability, and describes the so called "Proportionate Response" between the magnetic permeability and the applied strain. The invention according to the fourth aspect is advantageous primarily because the inventors have surprisingly found that by adjusting the composition of the fibre, particularly by increasing the level of silicon, the proportionate response is dramatically enhanced. Therefore the magnetic sensitivity of the fibres to strain is greatly increased.

Silicon for the purposes of this invention is provided at a level within the fibre of preferably approximately 3% to approximately 5%, more preferably at a level of approximately 4% to approximately 5%.

The fibre may also comprise further alloying additions of Phosphorus.

Phosphorous for the purposes of this invention is provided at a level within the fibre of approximately 0.001% to approximately 0.1%, preferably approximately 0.01% to approximately 0.07%, more preferably at a level of approximately 0.04% to approximately 0.06%.

The fibre may also comprise further alloying additions of Sulphur.

Sulphur for the purposes of this invention is provided at a level within the fibre of approximately 0.001% to approximately 0.1%, preferably approximately 0.01% to approximately 0.07%, more preferably at a level of approximately 0.02% to approximately 0.04%.

Carbon for the purposes of this invention is provided at a level within the fibre of approximately 0.1% to approximately 1%, preferably approximately 0.15% to approximately 0.20%, more preferably at a level of approximately 0.18% to approximately 0.19%.

Manganese for the purposes of this invention is provided at a level within the fibre of approximately 0.1% to approximately 5%, preferably approximately 1% to approximately 2%, more preferably at a level of approximately 1.1% to approximately 1.3%.

Chromium for the purposes of this invention is provided at a level within the fibre of approximately 5% to approximately 17%, preferably approximately 10% to approximately 15%, more preferably at a level of approximately 13% to approximately 14%.

Nickel for the purposes of this invention is provided at a level within the fibre of approximately 0.1% to approximately 1%, preferably approximately 0.2% to approximately 0.3%, more preferably at a level of approximately 0.28% to approximately 0.29%.

The fibre when described with reference to the first, second or third aspects of the invention may be defined as the fibre according to the fourth aspect. Therefore the fibre of the fourth aspect may be used in the concrete of the first aspect, in the method of the second aspect, and in the use of the third aspect.

The fibre of the fourth aspect is suitable for inclusion within concrete.

The fibre is preferably heat treated prior to use, the temperature of the heat treatment being up to or including 500 C. This increases the measured magnetic response from the fibre over that achieved by the fibre alone without the heat treatment.

The fibres have a length of width dimensions as described above.

BRIEF DESCRIPTION OF THE DRAWINGS

The invention will now be described by way of example only with reference to the drawings in which.

Figure 4:
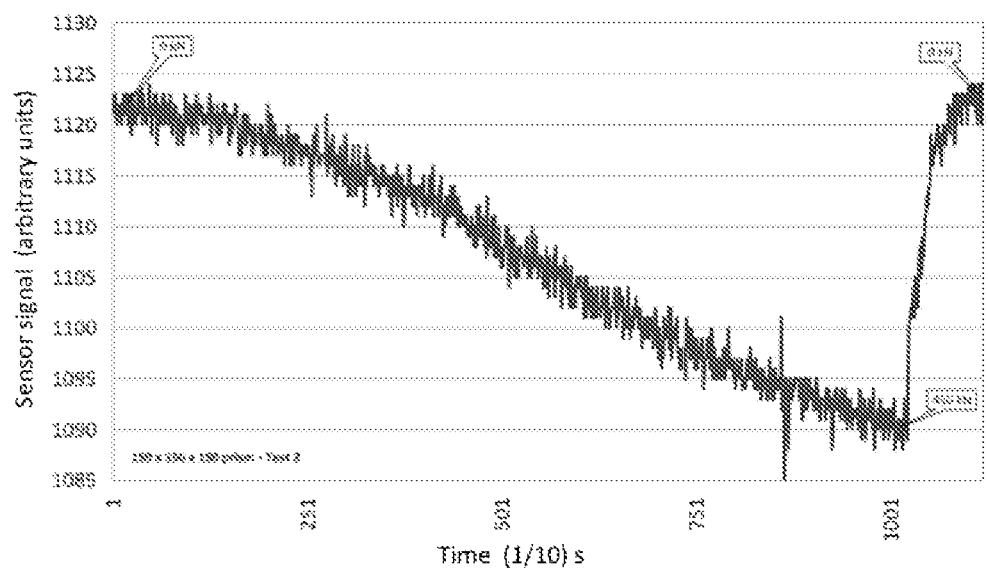
Figure 5:
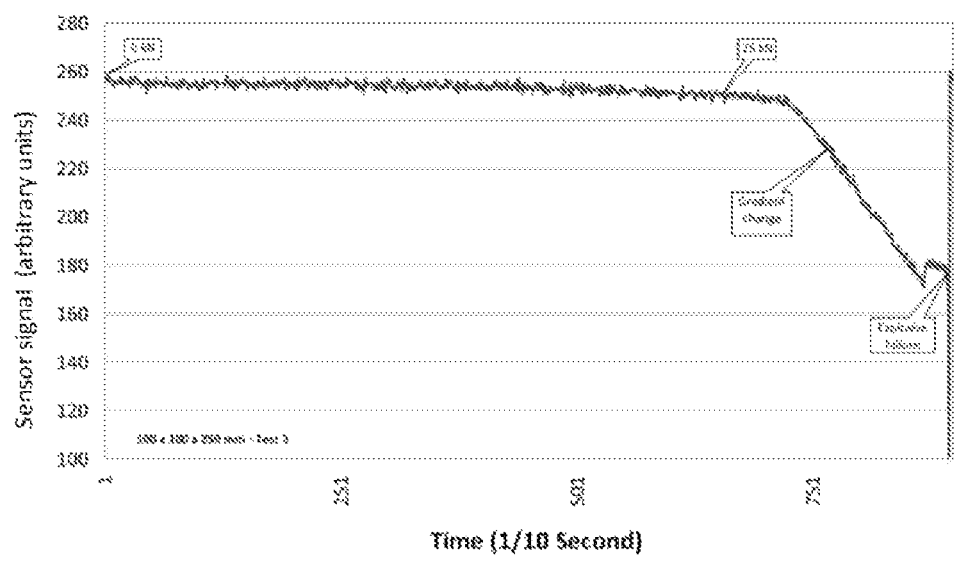

FIG. 4 is a graph showing the variation in magnetic permeability probe output during loading and unloading of a steel fibre reinforced concrete test prism (150×150×300 mm). Fourth cycle, continuous loading from 0-450 kN with subsequent slow load release; and FIG. 5 is a graph showing the variation in magnetic permeability probe output during loading of a steel fibre reinforced concrete test prism (100×100×250 mm). Single cycle of continuous loading from 0 kN with subsequent explosive failure occurring at 280 kN.

DETAILED DESCRIPTION OF THE INVENTION

The following is a description of an experimental study in which there is described an example embodiment of the invention.

Aim.

1. To demonstrate the use of an oscillating current field measurement probe for measuring the strain within the steel fibres embedded within reinforced concrete (SFRC); and 2. To determine if the signal produced during said use above correlates with an applied load on the concrete.

Materials and Methods

Two concrete test prism specimens (10) were manufactured. Sample A measured 150×150×300 mm and Sample B measured 100×100×250 mm. Both were manufactured using a Portland cement concrete mix containing 2% (by volume) of 30 mm long ferromagnetic stainless steel fibre. The steel fibre had a composition that included iron with alloying additions in weight % of typically 0.4% Carbon, 4.5% Silicon, 2% Manganese, and 14% Chromium with further additions of 0.050% Phosphorus, and 0.03% Sulphur. The concrete (10) was designed to have a characteristic strength of 32 MPa and employed a Thames Valley gravel aggregate with a maximum size of 20 mm and cement content of 325 kg/m$^3$. The initial plain concrete mix was manufactured using a conventional paddle mixer and once the main ingredients were well combined the steel fibres were added in increments and mixed until they were evenly distributed within the mass of fresh concrete. The resulting freshly mixed concrete had a measured slump of 30 mm and Vebe time of 4 seconds. The fresh concrete mix was cast into pre-oiled steel moulds on a standard casting table operating under constant vibration to ensure good compaction of the concrete. Care was taken to avoid any over-vibration of the fresh concrete which it is known can cause segregation of steel fibre reinforcement under certain circumstances. Once cast the samples (10) were stored at 100% RH and 20° C. for 24 hours after which the concrete prism specimens (10) were stripped from the moulds and stored under water at 20° C. for 27 days to ensure that the cement had time to hydrate satisfactorily.

Figure 1:
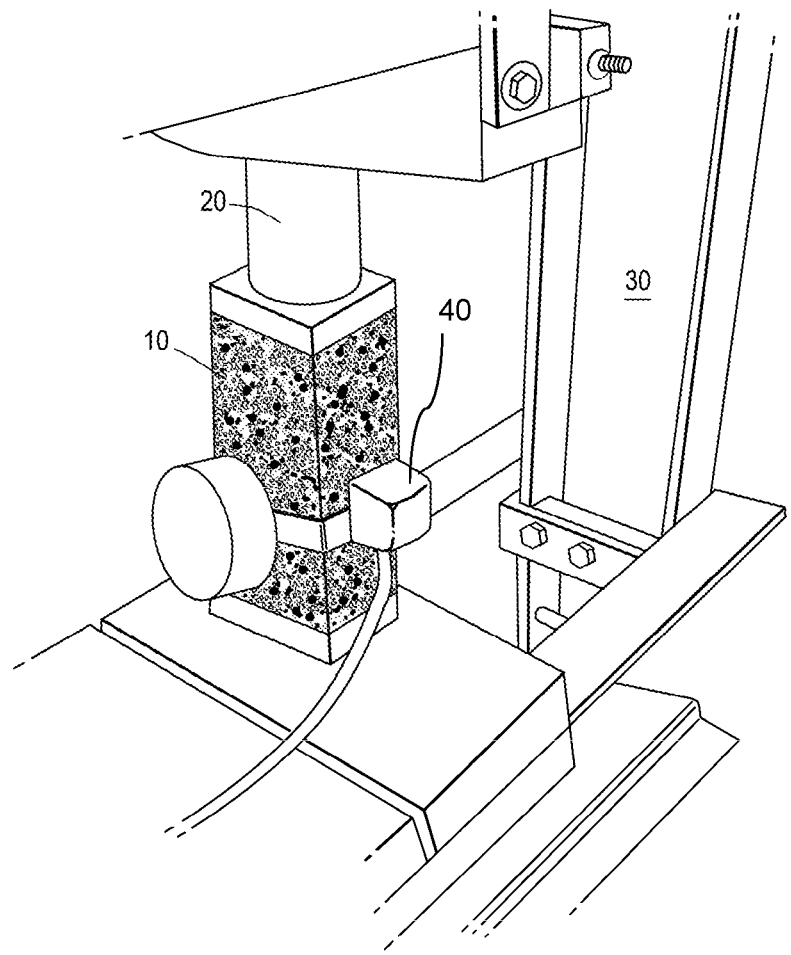
FIG. 1 shows a general test arrangement including a 100×100×250 mm steel fibre reinforced concrete test prism positioned within a loading frame with a magnetic permeability probe attached to front surface using a strap arrangement.

Testing involved uniaxial compressive loading of the test prisms (10) in a test frame (30) with a maximum load capacity of 50 kN. Loading was applied via a hand pumped hydraulic jack (20). The general test geometry is shown in FIG. 1.

Standard (unmodified) magnetic permeability probes (40) were attached to the surface of the prism (10) under test using a simple strap arrangement. The magnetic permeability probe (40) is an oscillating current field measurement probe for measuring strain in solely ferromagnetic metals. A hall probe may also be used in its place for the same function along with a permanent or electro magnet to induce the magnetic field within the concrete (10).

The signal from the transducer probe (40) was monitored using software developed for monitoring stresses and strains in steel structures. The output units are therefore arbitrary. Three tests were conducted.

Test 1—Prism Sample A was subjected to three loading cycles that were designed to ensure that the concrete remained below 60% of its ultimate strength and so would be operating within its elastic region allowing repeated loading and unloading without any damage accumulation. The first cycle consisted of continuous (slow) loading from 0-300 kN with subsequent quick load release. The second cycle consisted of continuous (fast) loading from 0-300 kN with subsequent quick load release. The third cycle consisted of continuous (fast) loading from 0-300 kN followed by (slow) loading from 300-450 kN with subsequent slow load release. FIG. 1 shows a general test arrangement including a 100×100×250 mm steel fibre reinforced concrete test prism positioned within a loading frame with a magnetic permeability probe attached to front surface using a strap arrangement.

Figure 3:
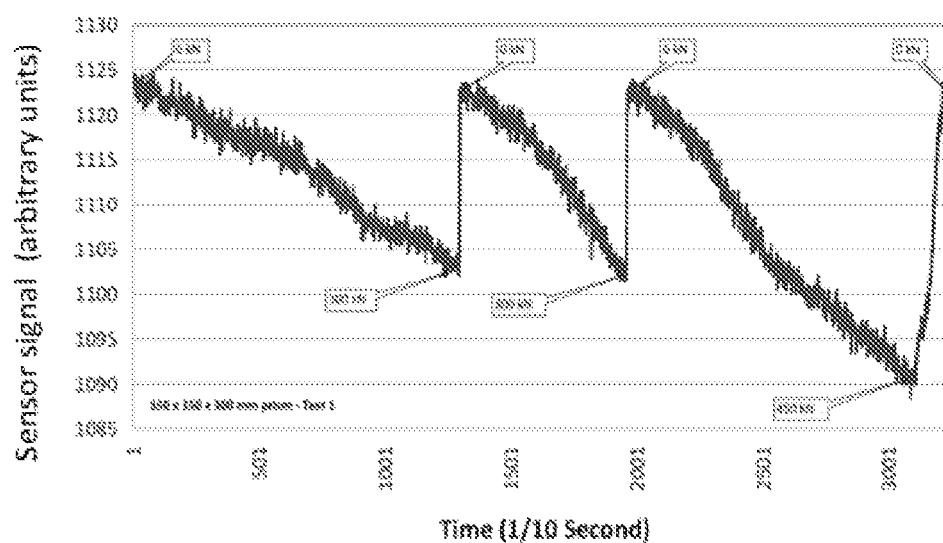
FIG. 3 is a graph showing the variation in the magnetic permeability probe output during loading and unloading of a steel fibre reinforced concrete test prism (150×150×300 mm). First cycle, continuous (slow) loading from 0-300 kN with subsequent quick load release. Second cycle, continuous (fast) loading from 0-300 kN with subsequent quick load release. Third cycle, continuous (fast) loading from 0-300 kN and slow loading from 300-450 kN with subsequent slow load release.

See FIG. 3 for the results of test 1.

Test 2—Prism Sample A was subject to a single cycle consisting of continuous loading from 0-450 kN with subsequent slow load release. See FIG. 4 for the results.

Test 3—Prism Sample B was subject to a single cycle of continuous loading from 0-300 kN with explosive failure occurring at 270-280 kN.

Figure 2:
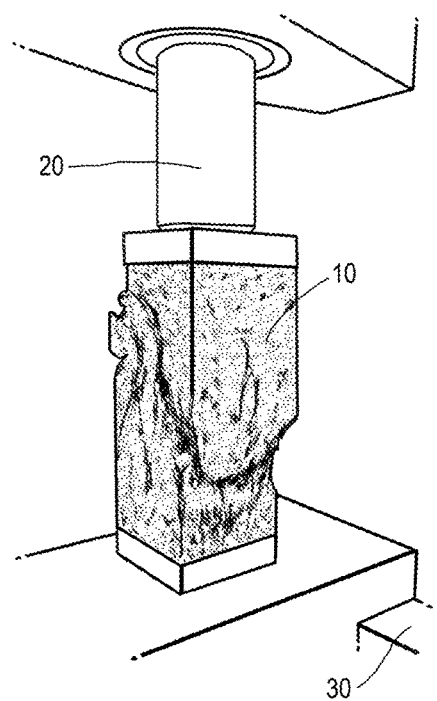
FIG. 2 shows the appearance of a test specimen following explosive failure showing presence of multiple "Poisson" splits on surface and revealing steel fibres.

FIG. 2 shows the appearance of a test specimen (10) following explosive failure (test 3) showing presence of multiple "Poisson" splits on surface and revealing steel fibres. See FIG. 5 for the results.

Discussion

Test 1—Considering the results presented it is clear that during the first cycle of loading of Sample A the output from the magnetic permeability probe transducer showed a steady decrease with time. Subsequent unloading of the specimen (by quickly releasing the pressure in the hand-pump) resulted in the magnetic permeability probe reading returning to its original value. The second loading cycle showed that this effect was reproducible and the values obtained from the transducer were essentially the same as that measured during the first cycle. The third cycle included a higher total load and after unloading the values from the measurement system had returned to that at the start of the first cycle. These results show that the magnetic permeability probe is capable of indicating the strain state of a concrete sample containing 0.5-5% ferromagnetic stainless steel fibres.

Test 2—Following Test 1 the test prism was left unloaded for a short time and the stability of the transducer system was found to be good. Subsequently, a repeat of the third cycle undertaken during the first set of tests was undertaken. The results from this test were in close agreement with that from the previous test cycle. Taken together these first two trials confirm that the combined fibre/transducer system is able to successfully and reproducibly reflect the strain state within the concrete section.

Test 3—This test aimed to explore the behaviour of the system at higher applied strain levels than those experienced in Test 1 and 2. To that end Specimen B was subject to continuous loading from 0-300 kN which was anticipated to be within 90% of the ultimate failure load of the specimen. However, the aspect ratio of the sample 100×100×250 mm coupled with asymmetry in the relatively low stiffness loading frame resulted in the specimen undergoing catastrophic explosive failure at 280 kN. FIG. 5 shows that the monitoring system was able to show that the sample response to loading was linear up to approximately 250 kN and that after that the signal showed a significantly increased rate of change prior to the eventual failure event. This is consistent with the initiation of transverse (tensile) Poisson splits which form and grow at right angles to the direction of loading (see FIG. 2). Indeed the initiation and growth of growth of tensile cracks is likely to be resisted by the presence of steel fibres within the concrete which, as they attempt to bridge the cracks, will be subject to increased strain levels. Thus, this result suggests that the combination fibres and sensor technology employed are capable of detecting the earliest stages of micro crack formation within concrete.

Conclusions

This study offers a non-destructive system capable of measuring both elastic strain distributions in concrete structures and detecting the formation of unstable micro-cracks prior to their growth and catastrophic failure. The inventors have been surprised by this study as the range of conventional magnetic sensing methods and the density and non-conductivity of concrete would be expected to rule out using magnetic methods to detect strain in concrete. The inventors are further surprised because the results have shown that magnetic methods which are conventionally used on solid metal structures, can be used to measure changes in the strain experienced (and load carried) in concrete structures containing melt extracted ferromagnetic SFRC structures with low volumetric loadings of fibres (0.5-5%). It is not expected to be able to detect anything at such low percentages of fibre inclusion and especially when they are embedded within a non-metallic material which is dense and non-conductive.

In another example of the method the invention the concrete materials are formed substantially as described above containing the ferromagnetic steel fibres. The method for measuring the magnetic permeability is substantially the same also, but instead of using a magnetic permeability probe a Hall Probe is used. For this an electromagnet or permanent magnet is placed to one side of the concrete samples, and the Hall probe attached to the opposite side. The Hall probe measures the induced magnetism within the concrete as provided by the electromagnet.

Examples of the Ferromagnetic Fibre

Four examples of ferromagnetic fibre were produced. The production process was one of melt extraction which is a rapid solidification process carried out by the insertion of a short segmented rotating chill block into a bath of molten metal or alloy to produce fibres, filaments or ribbons directly from the molten pool. The quench rate was of the order 10,000-1,000,000 degrees C. per second to improve mechanical and chemical homogeneity of the alloy in the as cast condition.

For each example around 25 KG was produced. The samples were labelled HT1, HT2, HT3 and HT4, and analysis of the Carbon, Silicon, Manganese, Chromium and Nickle contents was performed. The results of the analysis are shown below in Table 1.

TABLE 1

Analysis results of the alloy ingredients of samples HT1-4.

| Sample | C (%) | Si (%) | Mn (%) | Cr (%) | Ni (%) |
| --- | --- | --- | --- | --- | --- |
| HT1 | 0.18 | 3.24 | 1.22 | 13.64 | 0.29 |
| HT2 | 0.19 | 3.86 | 1.19 | 13.52 | 0.29 |
| HT3 | 0.19 | 4.27 | 1.17 | 13.56 | 0.29 |
| HT4 | 0.18 | 4.64 | 1.14 | 13.58 | 0.29 |

Experiments to determine the proportionate response of each sample shown in Table 1.

A sample of each of the fibres HT1 and HT4 were individually tested to determine their proportionate response. This was measured as a calibration factor which was equal to the ratio of the magnetic response measured to the strain applied. To conduct each experiment a group of 20 fibres were lined up and glued onto a plastic substrate. The substrate was then placed in a bending rig in order to apply a controllable strain on the fibres up to 0.5%. The magnetic response was measured before and after bending using a magnetic permeability probe, but might also be measured using a Hall probe. The bending rig was able to provide data on the strain applied. The higher the calibration factor the greater the magnetic response measured, and therefore the more sensitive the fibres are to the induced magnetism.

Along with the samples described above, a mild steel patch sample was also tested to provide an indication of the top baseline value that might be obtained.

Sample HT1 (Si content 3.24%) showed a calibration factor of 0.11 which increased to 0.2 for HT4 (Si content 4.64%). This is compared to the results for the mild steel patch which produced a calibration factor of 0.32. The silicon content of the fibres therefore had a substantial and surprising effect on the proportionate magnetic response and dramatically increased the measured magnetic response. This is contrary to what one would expect to find when employing alloys with increasing amounts of combination elements. It is also contrary to what you would expect to find by increasing the silicon content which would make the fibres brittle conventionally.

The same experiment was performed on three individual batches of HT1. However in this experiment, the first batch was heated to 500 C for two hours, the second batch to 605 C for two hours and the third batch to 650 C for two hours. For the first batch the calibration factor rose again further to 0.26, which is an even more marked increase. However the second batch only produced a calibration factor of 0.13, and the third batch only produced a calibration factor of 0.11, which is no change. Therefore heating the fibre therefore causes further surprising increases in magnetic permeability, and results in a calibration factor which approaches that of mild steel. But heating the fibre over 500 C causes no change.

In the examples described above the fibres tested were 25 mm long each. A further experiment was conducted on an equivalent sample to HT1, but 35 mm long. Results shows a calibration factor of 0.04 was achieved which shows that the magnetic response to strain markedly reduces with increased length of the fibre.

What is claimed is:

1. A method for measuring strain within a concrete material, the method comprising:
   a) forming solid concrete containing between 0.5% and 10% ferro-magnetic fibres in a random distribution throughout the concrete;
   b) applying a magnetic field to the surface of the concrete to induce a magnetization within the concrete; and
   c) measuring the magnetization within the concrete induced by the magnetic field.

2. The method according to claim 1, wherein the ferro-magnetic fibres are stainless steel.

3. The method according to claim 1, wherein the ferro-magnetic fibres are 20 to 50 mm long.

4. The method according to claim 1, wherein the fibres have a width of up to 4 mm.

5. The method according claim 1, wherein the concrete comprises an aggregate content with a maximum size of 20 mm.

6. The method according to claim 1, wherein steps b) and c) are performed using a magnetic permeability probe.

7. The method according to claim 1, wherein in step b) the magnetic field is applied by placing a current carrying coil or permanent magnet in contact with or close to the fibre containing concrete.

8. The method according to claim 7, wherein the magnetic field applied is an oscillating, static, or quasi-static electromagnetic field.

9. The method according to claim 7, wherein in step c) the measurement of the magnetization within the fibre containing concrete is performed by using a Hall probe or by measuring reactance in the current carrying coil.

* * * * *